US007649018B2

(12) United States Patent
Fawzi et al.

(10) Patent No.: US 7,649,018 B2
(45) Date of Patent: Jan. 19, 2010

(54) MONO- AND DI-PHOSPHATES OF 3-(3-FLUORO-4-HYDROXY-PHENYL)-7-HYDROXY-NAPHTHALENE-1-CARBONITRILE

(75) Inventors: Mahdi B. Fawzi, Morristown, NJ (US); Parimal R. Desai, Nanuet, NY (US); Tianmin Zhu, Monroe, NY (US)

(73) Assignee: Wyeth LLC, Madison, NJ (US)

( * ) Notice: Subject to any disclaimer, the term of this patent is extended or adjusted under 35 U.S.C. 154(b) by 141 days.

(21) Appl. No.: 12/034,052

(22) Filed: Feb. 20, 2008

(65) Prior Publication Data

US 2008/0214507 A1 Sep. 4, 2008

Related U.S. Application Data

(60) Provisional application No. 60/902,460, filed on Feb. 21, 2007.

(51) Int. Cl.
*C07C 255/52* (2006.01)

(52) U.S. Cl. ....................................... 514/520; 558/303

(58) Field of Classification Search ................. 558/303; 514/520

See application file for complete search history.

(56) References Cited

U.S. PATENT DOCUMENTS

2003/0181519 A1 9/2003 Mewshaw et al.

OTHER PUBLICATIONS

ISR for PCT US2008/054381, Jul. 11, 2008.

Mewshaw, R.E., et al., "ERbeta ligands. 3. Exploiting two binding orientations of the 2-phenylnapthalene scaffold to achieve ERbeta selectivity", Journal of Medicinal Chemistry, 48(12):3953-3979, 2005.

*Primary Examiner*—Kamal A Saeed
*Assistant Examiner*—Samantha L Shterengarts
(74) *Attorney, Agent, or Firm*—Pepper Hamilton LLP

(57) ABSTRACT

Compounds of formula II

Figure 1:
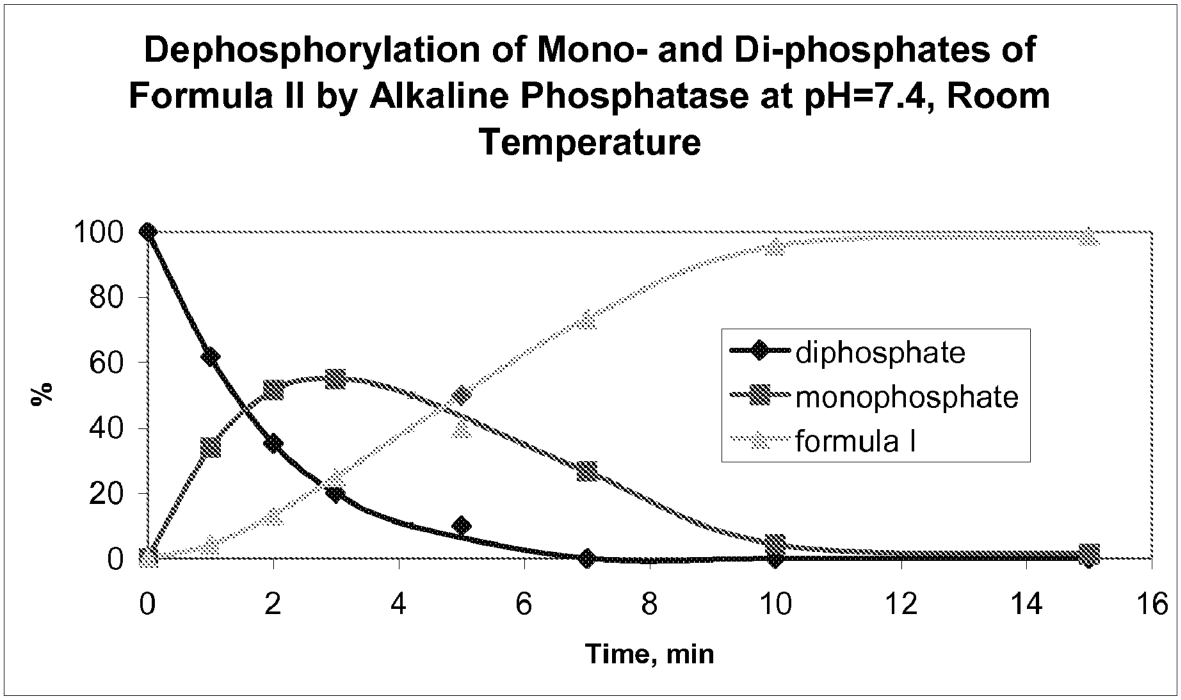

II wherein each $R^1$ and $R^2$ is independently selected from H and —P(O)($R^3$)($R^4$), provided that at least one of $R^1$ and $R^2$ is —P(O)($R^3$)($R^4$);

each $R^3$ and $R^4$ is independently selected from the group consisting of H, —OH, $C_1$-$C_6$ alkyl, and $C_1$-$C_6$ alkoxy;

or a pharmaceutically acceptable salt thereof. Pharmaceutical compositions comprising a compound of formula II, and methods of administering such compounds and compositions.

26 Claims, 1 Drawing Sheet

MONO- AND DI-PHOSPHATES OF 3-(3-FLUORO-4-HYDROXY-PHENYL)-7-HYDROXY-NAPHTHALENE-1-CARBONITRILE

This application claims benefit of priority to U.S. provisional patent application Ser. No. 60/902,460 filed Feb. 21, 2007, which is hereby incorporated by reference in its entirety.

FIELD OF THE INVENTION

The present invention relates to mono- and di-phosphates of 3-(3-fluoro-4-hydroxyphenyl)-7-hydroxynaphthonitrile and methods of administering 3-(3-fluoro-4-hydroxyphenyl)-7-hydroxynaphthonitrile by administering such phosphates to a patient in need thereof.

BACKGROUND OF THE INVENTION

The pleiotropic effects of estrogens in mammalian tissues have been well documented, and it is now appreciated that estrogens affect many organ systems [Mendelsohn and Karas, New England Journal of Medicine 340: 1801-1811 (1999), Epperson, et al., Psychosomatic Medicine 61: 676-697 (1999), Crandall, Journal of Womens Health & Gender Based Medicine 8: 1155-1166 (1999), Monk and Brodaty, Dementia & Geriatric Cognitive Disorders 11: 1-10 (2000), Hum and Macrae, Journal of Cerebral Blood Flow & Metabolism 20: 631-652 (2000), Calvin, Maturitas 34: 195-210 (2000), Finking, et al., Zeitschrift fur Kardiologie 89: 442-453 (2000), Brincat, Maturitas 35: 107-117 (2000), Al-Azzawi, Postgraduate Medical Journal 77: 292-304 (2001)]. Estrogens can exert effects on tissues in several ways, and the most well characterized mechanism of action is their interaction with estrogen receptors leading to alterations in gene transcription. Estrogen receptors are ligand-activated transcription factors and belong to the nuclear hormone receptor superfamily. Other members of this family include the progesterone, androgen, glucocorticoid and mineralocorticoid receptors. Upon binding ligand, these receptors dimerize and can activate gene transcription either by directly binding to specific sequences on DNA (known as response elements) or by interacting with other transcription factors (such as AP1), which in turn bind directly to specific DNA sequences [Moggs and Orphamides, EMBO Reports 2: 775-781 (2001), Hall, et al., Journal of Biological Chemistry 276: 36869-36872 (2001), McDonnell, Principles Of Molecular Regulation. p 351-361 (2000)]. A class of "coregulatory" proteins can also interact with the ligand-bound receptor and further modulate its transcriptional activity [McKenna, et al., Endocrine Reviews 20: 321-344 (1999)]. It has also been shown that estrogen receptors can suppress NF.kappa.B-mediated transcription in both a ligand-dependent and independent manner [Quaedackers, et al., Endocrinology 142: 1156-1166 (2001), Bhat, et al., Journal of Steroid Biochemistry & Molecular Biology 67: 233-240 (1998), Pelzer, et al., Biochemical & Biophysical Research Communications 286: 1153-7 (2001)].

Estrogen receptors can also be activated by phosphorylation. This phosphorylation is mediated by growth factors such as EGF and causes changes in gene transcription in the absence of ligand [Moggs and Orphamides, EMBO Reports 2: 775-781 (2001), Hall, et al., Journal of Biological Chemistry 276: 36869-36872 (2001)].

A less well-characterized means by which estrogens can affect cells is through a so-called membrane receptor. The existence of such a receptor is controversial, but it has been well documented that estrogens can elicit very rapid nongenomic responses from cells. The molecular entity responsible for transducing these effects has not been definitively isolated, but there is evidence to suggest it is at least related to the nuclear forms of the estrogen receptors [Levin, Journal of Applied Physiology 91: 1860-1867 (2001), Levin, Trends in Endocrinology & Metabolism 10: 374-377 (1999)].

Two estrogen receptors have been discovered to date. The first estrogen receptor was cloned about 15 years ago and is now referred to as ERα [Green, et al., Nature 320: 134-9 (1986)]. The second form of the estrogen receptor was found comparatively recently and is called ERβ [Kuiper, et al., Proceedings of the National Academy of Sciences of the United States of America 93: 5925-5930 (1996)]. Early work on ERβ focused on defining its affinity for a variety of ligands and indeed, some differences with ERα were seen. The tissue distribution of ERβ has been well mapped in the rodent and it is not coincident with ERα. Tissues such as the mouse and rat uterus express predominantly ERα, whereas the mouse and rat lung express predominantly ERβ [Couse, et al., Endocrinology 138: 4613-4621 (1997), Kuiper, et al., Endocrinology 138: 863-870 (1997)]. Even within the same organ, the distribution of ERα and ERβ can be compartmentalized. For example, in the mouse ovary, ERβ is highly expressed in the granulosa cells and ERα is restricted to the thecal and stromal cells [Sar and Welsch, Endocrinology 140: 963-971 (1999), Fitzpatrick, et al., Endocrinology 140: 2581-2591 (1999)]. However, there are examples where the receptors are coexpressed and there is evidence from in vitro studies that ERα and ERβ can form heterodimers [Cowley, et al., Journal of Biological Chemistry 272: 19858-19862 (1997)].

A large number of compounds have been described that either mimic or block the activity of 17β-estradiol. Compounds having roughly the same biological effects as 17β-estradiol, the most potent endogenous estrogen, are referred to as "estrogen receptor agonists". Those which, when given in combination with 17β-estradiol, block its effects are called "estrogen receptor antagonists". In reality there is a continuum between estrogen receptor agonist and estrogen receptor antagonist activity and indeed some compounds behave as estrogen receptor agonists in some tissues and estrogen receptor antagonists in others. These compounds with mixed activity are called selective estrogen receptor modulators (SERMS) and are therapeutically useful agents (e.g. EVISTA) [McDonnell, Journal of the Society for Gynecologic Investigation 7: S10-S15 (2000), Goldstein, et al., Human Reproduction Update 6: 212-224 (2000)]. The precise reason why the same compound can have cell-specific effects has not been elucidated, but the differences in receptor conformation and/or in the milieu of coregulatory proteins have been suggested.

It has been known for some time that estrogen receptors adopt different conformations when binding ligands. However, the consequence and subtlety of these changes has been only recently revealed. The three dimensional structures of ERα and ERβ have been solved by co-crystallization with various ligands and clearly show the repositioning of helix 12 in the presence of an estrogen receptor antagonist which sterically hinders the protein sequences required for receptor-coregulatory protein interaction [Pike, et al., Embo 18: 4608-4618 (1999), Shiau, et al., Cell 95: 927-937 (1998)]. In addition, the technique of phage display has been used to identify peptides that interact with estrogen receptors in the presence of different ligands [Paige, et al., Proceedings of the National Academy of Sciences of the United States of America 96: 3999-4004 (1999)]. For example, a peptide was identified that distinguished between ERα bound to the full estrogen receptor agonists 17β-estradiol and diethylstilbesterol. A different peptide was shown to distinguish between clomiphene bound to ERα and ERβ. These data indicate that each ligand potentially places the receptor in a unique and unpredictable conformation that is likely to have distinct biological activities.

As mentioned above, estrogens affect a panoply of biological processes. In addition, where gender differences have been described (e.g. disease frequencies, responses to challenge, etc), it is possible that the explanation involves the difference in estrogen levels between males and females.

The preparation and use of 3-(3-fluoro-4-hydroxyphenyl)-7-hydroxynaphthonitrile as a therapeutic estrogenic agent is reported in U.S. Pat. No. 6,914,074. New and better methods of delivering therapeutic compounds are always in demand. Accordingly, the compounds and methods described herein, provide means for delivering the estrogenic agent to a patient in need thereof.

SUMMARY OF THE INVENTION

Some embodiments of the invention provide a compound of formula II

II

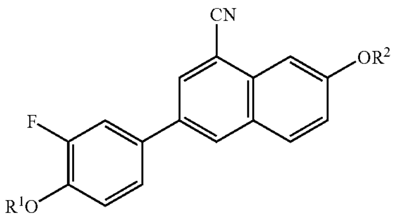

wherein each $R^1$ and $R^2$ is independently selected from H and —$P(O)(R^3)(R^4)$, provided that at least one of $R^1$ and $R^2$ is —$P(O)(R^3)(R^4)$;

each $R^3$ and $R^4$ is independently selected from the group consisting of H, —OH, $C_1$-$C_6$ alkyl, and $C_1$-$C_6$ alkoxy;

or a pharmaceutically acceptable salt thereof.

In some embodiments, each of $R^1$ and $R^2$ is —$P(O)(R^3)(R^4)$.

In some embodiments, each $R^3$ and $R^4$ is —OH.

In some embodiments, the compound of formula II, is provided wherein $R^1$ and $R^2$ is —$P(O)(R^3)(R^4)$ and each $R^3$ and $R^4$ is independently $C_1$-$C_6$ alkyl or $C_1$-$C_6$ alkoxy.

In some embodiments, the each $R^3$ and $R^4$ are the same.

Some embodiments of the invention provide a pharmaceutical composition comprising a compound of formula II as described herein or a pharmaceutically acceptable salt thereof and a pharmaceutically acceptable carrier or excipient.

In some embodiments, the invention provides methods for treating or inhibiting sepsis in a patient in need thereof, comprising administering a pharmaceutically effective amount of a compound of formula II or a pharmaceutically acceptable salt thereof.

In some embodiments, the invention provides methods for treating or inhibiting rheumatoid arthritis in a patient in need thereof, comprising administering a pharmaceutically effective amount of a compound of formula II or a pharmaceutically acceptable salt thereof.

In some embodiments, the invention provides methods for treating or inhibiting endometriosis in a patient in need thereof, comprising administering a pharmaceutically effective amount of a compound of formula II or a pharmaceutically acceptable salt thereof.

In some embodiments, the invention provides methods for treating or inhibiting fibroids in a patient in need thereof, comprising administering a pharmaceutically effective amount of a compound of formula II or a pharmaceutically acceptable salt thereof.

Some embodiments provide a method of administering a compound of formula I

I

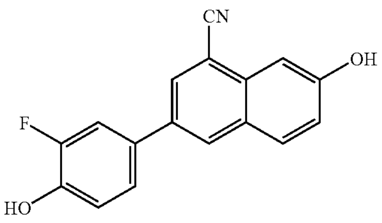

comprising administering to a patient in need thereof a pharmaceutically effective amount of a compound of formula II as described herein or a pharmaceutically acceptable salt thereof.

Other embodiments of the invention which do not differ significantly from the scope and spirit of this disclosure will be apparent to those of skill in the art and are considered part of the invention disclosed herein.

BRIEF DESCRIPTION OF THE DRAWING FIGURE

The sole drawing FIGURE is a graph depicting the percent dephosphorylation of mono- and di phosphates according to some embodiments of the invention over time.

DETAILED DESCRIPTION OF THE INVENTION

As used herein, the term "providing," with respect to providing a compound or substance described herein to a patient, means either directly administering such a compound or substance, or administering a prodrug, derivative, or analog which will form the effective amount of the compound or substance within the body.

As used herein the terms "treatment", "treating", "treat" and the like refer to obtaining a desired pharmacologic and/or physiologic effect. The effect may be therapeutic in terms of a partial or complete stabilization or cure for a disease and/or adverse effect attributable to the disease. "Treatment" or "treating" as used herein covers any treatment of a disease in a subject, particularly a human, and includes: (a) inhibiting the disease; for example, inhibiting a disease, condition, disorder, or one or more symptoms thereof, in an individual who is experiencing or displaying the pathology or symptomatology of the disease, condition or disorder (i.e., arresting, retarding, or restraining further development of the pathology and/or symptomatology; or relieving a disease symptom, i.e., causing regression of the disease or symptom; and (b) ameliorating the disease; for example, ameliorating a disease, condition, disorder, or one or more symptoms thereof in an individual who is experiencing or displaying the pathology or symptomatology of the disease, condition or disorder (i.e., reversing the pathology and/or symptomatology).

As used herein, the term "inhibit" and other forms thereof means arresting, retarding, or restraining a disease (including one or more symptoms thereof), condition or disorder in an individual who is experiencing or displaying the pathology or symptomatology of the disease, condition or disorder (i.e., arresting, retarding, or restraining further development of the pathology and/or symptomatology) or relieving the disease symptom, i.e., causing regression of the disease or symptom.

As used herein, the term "alkyl" refers to a saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. Alkyl groups can contain from 1 to about 20, 1 to about 10, 1 to about 8, 1 to about 6, 1 to about 4, or 1 to about 3 carbon atoms. In some embodiments, alkyl groups can be substituted with up to four independently selected substituents.

As used herein, "alkoxy" refers to an —O-alkyl group. Example alkoxy groups include methoxy, ethoxy, propoxy (e.g., n-propoxy and isopropoxy), t-butoxy, and the like. An alkoxy group can contain from 1 to about 20, 1 to about 10, 1 to about 8, 1 to about 6, 1 to about 4, or 1 to about 3 carbon atoms. In some embodiments, alkoxy groups can be substituted with up to four independently selected substituents.

The designation $C_x$-$C_y$ indicates a carbon chain having from x to y carbon atoms, where x and y are integers.

This invention provides compounds which are mono- or di-phosphates of the compound of formula I

I

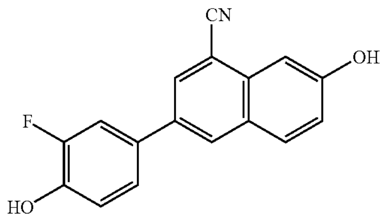

(3-(3-fluoro-4-hydroxyphenyl)-7-hydroxynaphthonitrile). These phosphates have general formula II:

II

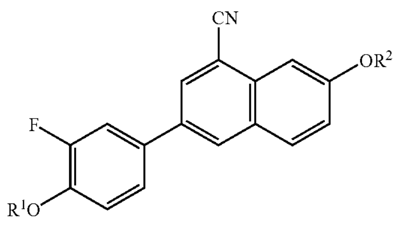

wherein each $R^1$, and $R^2$ is independently selected from H and —P(O)($R^3$)($R^4$), provided that at least one of $R^1$ and $R^2$ is —P(O)($R^3$)($R^4$);

each $R^3$ and $R^4$ is independently selected from the group consisting of H, —OH, $C_1$-$C_6$ alkyl, and $C_1$-$C_6$ alkoxy;

or a pharmaceutically acceptable salt thereof.

The mono-phosphates are those where only one of $R^1$ or $R^2$ is P(O)$R^3R^4$. The monophosphates are compounds according to formulas III and IV:

III

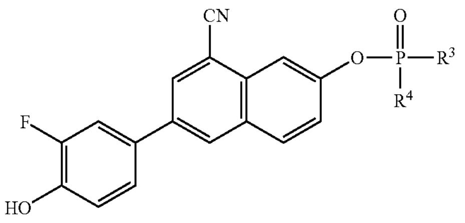

IV

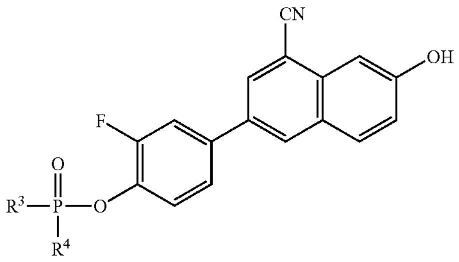

where $R^3$ and $R^4$ are as defined above. In some embodiments, $R^3$ and $R^4$ are the same. In some embodiments, $R^3$ and $R^4$ are OH. In some embodiments, each $R^3$ and $R^4$ is independently $C_1$-$C_6$ alkyl or $C_1$-$C_6$ alkoxy.

When both $R^1$ and $R^2$ are P(O)$R^3R^4$, the di-phosphate is formed. The diphosphates are compounds according to formula V:

V

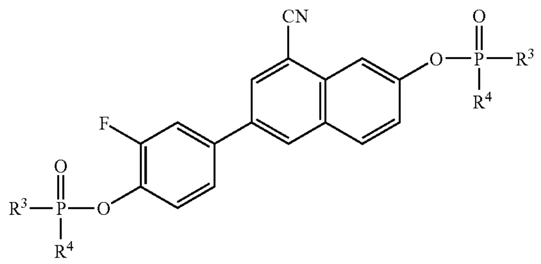

where $R^3$ and $R^4$ are as defined above. In some embodiments, $R^3$ and $R^4$ are the same. In some embodiments, $R^3$ and $R^4$ are OH. In some embodiments, each $R^3$ and $R^4$ are independently $C_1$-$C_6$ alkyl or $C_1$-$C_6$ alkoxy. In some embodiments, each $R^3$ and $R^4$ are the same.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1-6 carbon atoms or dialkylammonium salts containing 1-6 carbon atoms in each alkyl group, and trialkylammonium salts containing 1-6 carbon atoms in each alkyl group, when a compound of this invention contains an acidic moiety.

The phosphates described herein are useful as estrogenic agents, because they metabolize into the compound of formula I, which has been shown to be useful as an estrogenic agent for the treatment of many diseases, disorders, or conditions associated with menopausal, peri-menopausal, and post menopausal women. As such, the compounds of formula II and more specifically those of formulas III, IV and V may be used to administer a compound of formula I to a patient in need thereof.

Methods of providing a compound of formula I, as defined above, comprise administering to a patient in need thereof a pharmaceutically effective amount of a compound of formula II, as defined above, or a pharmaceutically acceptable salt thereof. The method may also comprise administration of a pharmaceutical composition comprising a compound of formulas II, III, IV or V, or a pharmaceutically acceptable salt thereof, and a pharmaceutically acceptable carrier or excipient.

EXAMPLES 1 and 2

Synthesis of the Diphosphate Compounds

EXAMPLE 1

3-(3-Fluoro-4-hydroxy-phenyl)-7-hydroxy-naphthalene-1-carbonitrile, 1 ($C_{17}H_{10}FNO_2$, 2.78 g, 10 mmol) and tetrazole (4.2 g, 60 mmol) were dissolved in 100 ml 1:1 mixture of dry tetrahydrofuran and methylene chloride. Under the $N_2$ and stirring, di-tert-butyl diisopropyl-phosphoramidite was added and the reaction mixture was stirred overnight. Then 2 ml of 30% hydrogen peroxide was added and reaction was carried on for 30 min. Then the excess of hydrogen peroxide was reduced by 15 ml of saturated sodium metabisulfite in ice bath for 30 min. The reaction mixture was extracted with 100 ml of ethyl acetate and washed with 2×50 ml of sodium metabisulfite. The organic layer was dried over anhydrous sodium sulfate and removed by rotavap. About 5 g of oil material was obtained. From 0.5 g of oil material, 69.1 mg of pure intermediate 2 ($C_{33}H_{44}FNO_8P_2$, $[M+NH4]^+$ 681) was obtained after prep HPLC (Luna 50×250 mm, $C_{18}(2)$, 10 um, 100 A, isocratic, 100 mL/min, 20% 20 mM, $NH_4Ac$, pH=4.5 and 80% ACN. Retention time, 18 min). 30 mg of intermediate was put into 5 ml of ethyl acetate and 3 drops of 37% HCl (about 300 ul). After 1 hour, the sample was put into speedvac for overnight. A total of 21 mg of white solid was obtained.

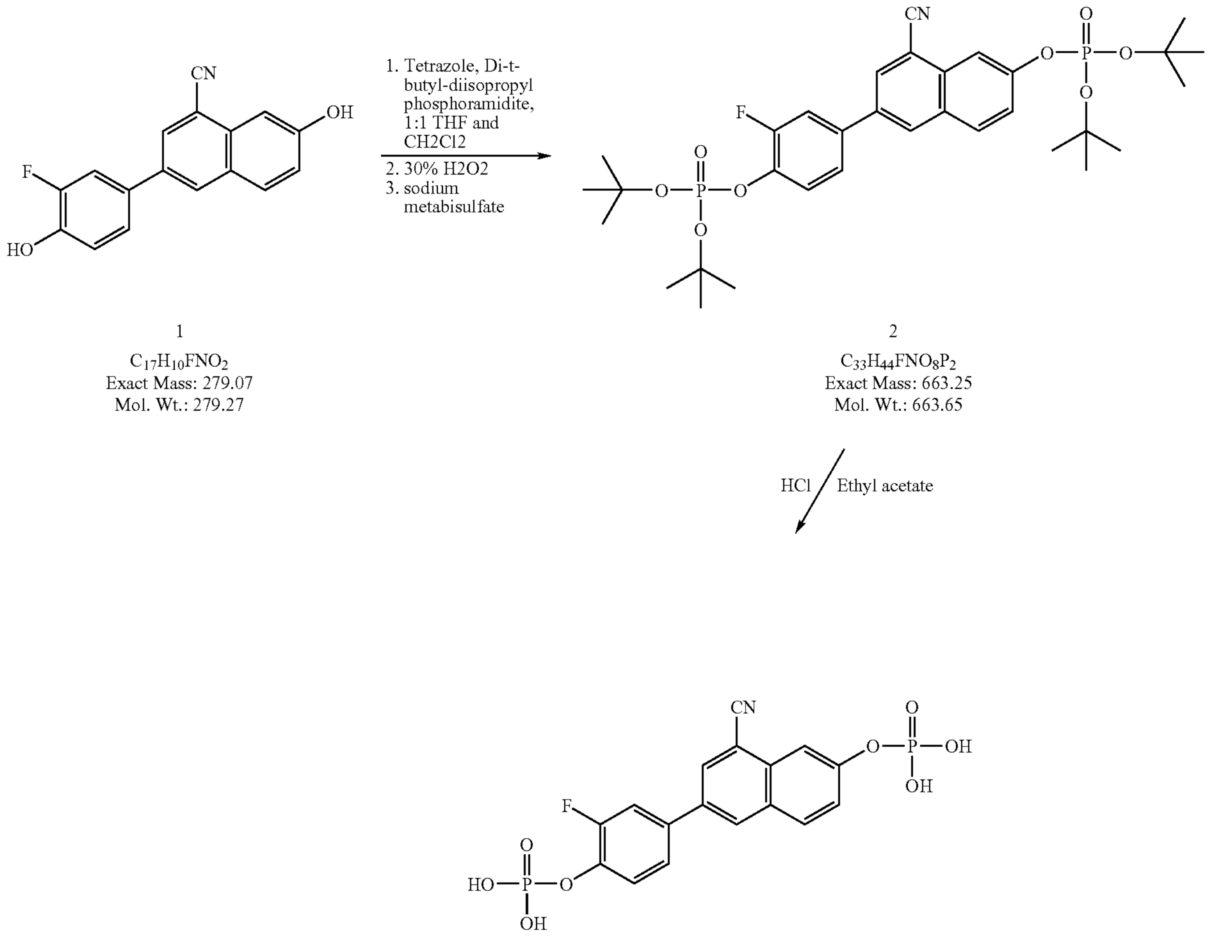

1

$C_{17}H_{10}FNO_2$
Exact Mass: 279.07
Mol. Wt.: 279.27

2

$C_{33}H_{44}FNO_8P_2$
Exact Mass: 663.25
Mol. Wt.: 663.65

3

Prodrug of 1

$C_{17}H_{12}FNO_8P_2$
Exact Mass: 439.00
Mol. Wt.: 439.23

The structure of the compound 3 was characterized by HRMS (measured accurate mass: [M+NH4]+, 457.0376 amu, calculated accurate mass: 457.0360 amu, elemental composition: $C_{17}H_{16}N_2O_8FP_2$ error: 1.6 mDa) and NMR.

EXAMPLE 2

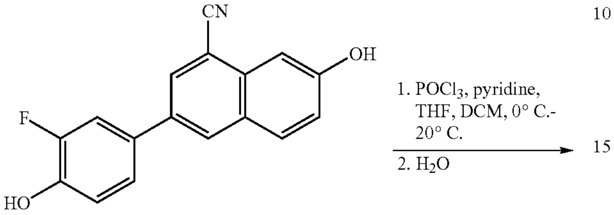

1

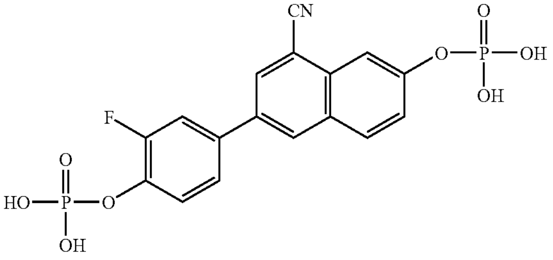

3

3-(3-Fluoro-4-hydroxy-phenyl)-7-hydroxy-naphthalene-1-carbonitrile, 1 (710 mg, 2.54 mmol), pyridine (1.0 mL, 12.0 mmol, 4.7 eq.) was dissolved in dichloromethane (5.0 mL). To a cold (0° C.) phosphorous oxychloride (0.90 mL, 9.6 mmol, 3.8 eq.) in DCM (20 mL), was added the above solution under $N_2$ at 0° C. over 30 minutes with stirring. The stirring was continued and the reaction was monitored by mass spectroscopy. Upon completion of phosphorylation, a solution of THF (15 mL) and water (15 mL) was added. Afterward, it was stirred at ambient temperature overnight. The solid formed was then collected by filtration and was uptaken into diluted aq. ammonium hydroxide to set PH=8. The solution was then poured into ethanol. The solid formed was collected by filtration. Product was further purified by repeating the above procedure for several times to give 700 (63%) mg of white solid.

EXAMPLE 3

Preparation of the Monophosphate Compounds

The monophosphate compounds were achieved by alkaline phosphatase digestion of the diphosphate compound 3 from above. About 150 mg of the diphosphate compound 3 were dissolved in 3-4 mL of water and pH was adjusted to 8 by TRIS. The enzyme was added gradually after checking the progress of the reaction by HPLC. When the level of monophosphates was about 30%, adding formic acid stopped the reaction. The reaction mixture was then injected on Gemini, C18, 5 um, 21.2×250 mm preparative column using 30 mM (NH4)2CO3, pH~9.1 (A) and ACN (B) mobile phase gradient (0 min 8% B, 1 min 8% B, then gradient to 12% B in 19 min). Two fractions of ERB-196-monophosphates were collected (Rt=~8 and 13 min) and then lyophilized to give total of 12 mg of monophosphate I [M−H]−=358 and 16 mg of monophosphate II [M−H]−=358.

Samples were dissolved in DMSO-d6. 1H and TOCSY experiments were performed with Bruker DRX-400 NMR instrument at 25° C. TMS was used as internal reference for proton (δ(1H)=0.0 ppm).

Structure elucidation revealed both structures and chemical shifts as presented below.

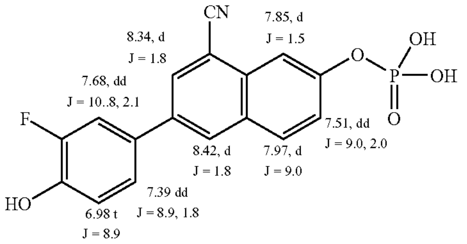

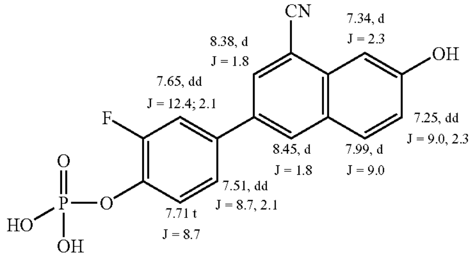

monophosphate II

Several exemplary compounds were subjected to in vitro and/or in vivo testing. Both in vitro and in vivo studies show that both mono-phosphate forms and the diphosphate form convert to the parent compound (formula I). Thus, these forms can be used to deliver effective amounts of the compound of formula I to a patient in need thereof.

In Vitro Enzyme Hydrolysis

Dephosphorylation of diphosphate compound 2 by alkaline phosphatase (Sigma, 1000 units, P-5521) at pH=7.4 (TRIS), room temperature.

1. 1 mg of diphosphate compound 2 was dissolved in 10 mL of TRIS buffer (20 mM, pH=7.4).

2. 250 uL of above solution (25 ug) was put into separate vials plus 250 ul of TRIS and 100 uL of enzyme solution. Enzyme solution is prepared by 5 uL of alkaline phosphatase diluting with TRIS (20 nM, pH=7.4) buffer to 1 ml.

3. The sample of 5 ul was taken at different time point and mixed with 5 uL of 0.5% TFA in acetonitrile to stop the enzyme reaction.

4. 5 uL was injected onto HPLC and analyzed using Luna C18, 4.6×250 mm column. Solvent system: A=$KH_2PO_4$/$K_2HPO_4$, 20 mM, pH=7, B=100% ACN. From 0 to 1 min 10% B, and then gradient to 90% B in 19 min. The peak area of original diphosphate compound, intermediate (both monophosphate compounds were co-eluted) and final product 3-(3-Fluoro-4-hydroxy-phenyl)-7-hydroxy-naphthalene-1-carbonitrile were integrated and plotted (see FIG. 1).

Diphosphate: Single Dose Intravenous (Bolus) Pharmacokinetic Study in Male BALB/c-Mice (Protocol 05_3039)

This study is designed to obtain relevant pharmacokinetic information following a single intravenous 15.7 mg/kg dose of Compound 3 in fed male BALB/c mice. This dose (15.7 mg/kg) of Compound 3 is chosen because it is equimolar to 10 mg/kg of Compound 1. The resulting PK data will be compared to the historical pharmacokinetic data following Compound 1 administration in BALB/c mice.

Preparation Procedures: An intravenous formulation will be made as a stock solution (10 mg/mL) one day prior to the start of dosing consisting of phosphate buffered saline adjusted to pH about 7.4 with NaOH. The dosing formulations will be prepared on the day of dosing by diluting the appropriate amount of the stock solution with D5W to obtain concentrations of 3.14 mg/mL of Compound 3 and then will be sterile filtered using a 0.20 micron filter about few hours prior to the start of dosing. The test formulation was stored at approximately 4° C. protected from light. The vehicle used for IV introduction was phosphate buffered saline consisting of 0.0144% (w/v) of KH2PO4, 0.90% (w/v) of NaCL, 0.0795% (w/v) of $Na_2HPO_4$, 0.325% of NaOH (1N) and 97.6811% sterile water for injection with the resulting pH of approximately 7.4. The stock solution (10 mg/mL) is stable for 7 days at 40 C.

The test formulation was administered once by a slow (approximately 10-15 seconds) intravenous bolus injection via the tail vein. The dose volumes was based on the most recent body weights.

This study is to be conducted in accordance with the PRACUC protocol entitled "Pharmacokinetics Following Oral (Gavage), Intravenous or Subcutaneous Administration of a Clinical Lead to Mice", approved by Wyeth Research, Pearl River Animal Care and Use Committee, PRACUC PROTOCOL NUMBER: 300014-978 (Expiration date: Jun. 24, 2006).

24 male Balb/c-mice were used in the study. Prior to randomization, each animal was numbered via an ear tag with a unique animal number (UAN), which was displayed on the cage card. After randomization, each test animal was assigned a study animal number (SAN). The cage card additionally contained the SAN, test article identification and dosage.

The mice were housed individually in polycarbonate cages containing contact bedding. As needed, the animals were removed from their normal housing conditions for sample collection or other special assessments as specified in this protocol or appropriate SOPs. Temperature was maintained at 72° F.±6° F. with a humidity of 50%±10%. Alternating 12-hour periods of light and dark were used, except for interruptions for brief periods, e.g., to facilitate eye examinations or sample collection). The commercial animal feed used is Purina Rodent Diet #5001 (pellets). Animals will be fed adlib. Drinking water was available ad libitum. Environment Individual body weights were obtained and recorded on the day of randomization (one day prior to dosing). Animal health checks (for moribundity and mortality) were done a minimum of once daily during the acclimation period and a minimum of once daily during conduct of the study. Animal observations for clinical signs of toxicity were not part of this study.

Blood samples were collected terminally from 3 isoflurane-anesthetized animals per time point using a non-serial bleeding design as follows:

| Sample Schedule (Time) | Animal Numbers 15.7 mg/kg |
|---|---|
| 0.25 hr | 1-3 |
| 0.5 hr | 4-6 |
| 1 hr | 7-9 |
| 2 hr | 10-12 |
| 5 hr | 13-15 |
| 8 hr | 16-18 |

-continued

| Sample Schedule (Time) | Animal Numbers 15.7 mg/kg |
|---|---|
| 12 hr | 19-21 |
| 24 hr | 22-24 |

Samples were taken via cardiac puncture using a stainless steel needle and appropriate size syringe. Each sample was transferred into a blood collection tube containing EDTA. Following sample collection, the animals were euthanized by exsanguination under $CO_2$ or isofluorane anesthesia.

Immediately after blood samples were collected, they were put on wet-ice until centrifugation at approximately 4° C. Plasma was separated, harvested by centrifugation of the blood samples at approximately 4° C., transferred into cryovac tubes, frozen on dry-ice and stored at approximately −70° C. prior to analysis.

Pharmacokinetic Analysis

LC/MS/MS was used in all 24 samples using a compound of formula I as the analyte. Pharmacokinetic (PK) parameters were calculated using IBIS (ver. 1.5.0) or WinNonlin (ver. 4.1) (if necessary). IBIS and WinNonlin use a non-compartmental model-independent approach. The following results indicate that the diphosphate Compound 3 converts to the parent compound 1.

1

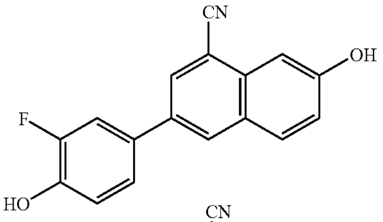

3

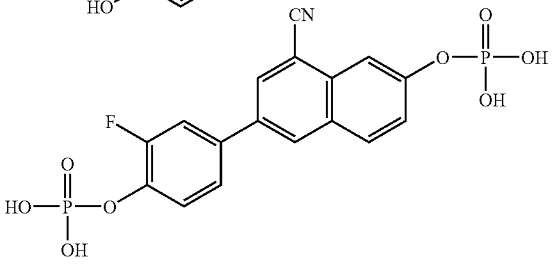

Mean (±SD) Plasma Compound 1 Concentrations (ng/mL) in Balb/C Mice Administered a Single 15.7 mg/kg Intravenous (Bolus) Dose of Diphosphate

| Compound 3 (Protocol 05_3039) | | | | | | | | | |
|---|---|---|---|---|---|---|---|---|---|
| Dosage | | Hours After Dosing | | | | | | | |
| (mg/kg) | SAN[a] | 0.25 | 0.5 | 1 | 2 | 5 | 8 | 12 | 24 |
| 15.7 | Mean | 1938 | 1160 | 274 | 176 | 133 | 62.2 | 3.90 | 0.0 |
| | SD | 223 | 472 | 146 | 24.0 | 163 | 51.3 | 6.75 | 0 |
| | n | 3 | 3 | 3 | 3 | 3 | 3 | 3 | 3 |

[a]Study animal number

Mean[a] Compound 1 Pharmacokinetic Parameters in Fasted BALB/c Male Mice Given a Single Intravenous 15.7 mg/kg Dose of Diphosphate Compound 3

(Protocol 05_3039)

| Dosage (mg/kg) | C5min (ng/mL) | AUC0-24 (ng · hr/mL) | AUC0-∞ (ng · hr/mL) | CLT (L/hr/kg) | Vdss (L/kg) | t½ (hr) |
|---|---|---|---|---|---|---|
| 15.7 | 1938 | 2367 | 2351 | 6.68 | 14.7 | 1.3 |

[a]Determined from the mean concentration-time profiles

Based on the results obtained in the standard pharmacological test procedures, the compounds of this invention are useful as pro-drugs of the compound of formula I, which is a known estrogenic agent useful in the treatment or inhibition of conditions, disorders, or disease states that are at least partially mediated by an estrogen deficiency or excess, or which may be treated or inhibited through the use of an estrogenic agent. The compounds of this invention, therefore, are useful in treating diseases, disorders, or conditions which may be treated with the compound of formula I.

In some embodiments, compounds of this invention are particularly useful in treating a peri-menopausal, menopausal, or postmenopausal patient. Menopause is generally defined as the last natural menstrual period and is characterized by the cessation of ovarian function, leading to the substantial diminution of circulating estrogen in the bloodstream. As used herein, menopause also includes conditions of decreased estrogen production that may be surgically, chemically, or be caused by a disease state which leads to premature diminution or cessation of ovarian function.

In some embodiments, compounds of this invention are also useful in inhibiting or treating other effects of estrogen deprivation including, hot flushes, vaginal or vulvar atrophy, atrophic vaginitis, vaginal dryness, pruritus, dyspareunia, dysuria, frequent urination, urinary incontinence, urinary tract infections. Other reproductive tract uses include the treatment or inhibition of dysfunctional uterine bleeding. The compounds are also useful in treating or inhibiting endometriosis.

In some embodiments, compounds of this invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. The compounds of this invention are also useful in treating or inhibiting benign or malignant abnormal tissue growth including, glomerulosclerosis, prostatic hypertrophy, uterine leiomyomas, breast cancer, scleroderma, fibromatosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

In some embodiments, compounds of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage.

In some embodiments, compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis, uveitis, psoriasis, multiple sclerosis, systemic lupus erythematosus and sepsis.

In some embodiments, compounds of this invention are also useful in treating or inhibiting ocular disorders including cataracts, uveitis, and macular degeneration and in treating skin conditions such as aging, alopecia, and acne.

In some embodiments, compounds of this invention are also useful in treating or inhibiting metabolic disorders such as type-II diabetes, of lipid metabolism, appetite (e.g. anorexia nervosa and bulimia).

In some embodiments, compounds in this invention are also useful in treating or inhibiting bleeding disorders such as hereditary hemorrhagic telangiectasia, dysfunctional uterine bleeding, and combating hemorrhagic shock.

In some embodiments, compounds of this invention are useful in disease states where amenorrhea is advantageous, such as leukemia, endometrial ablations, chronic renal or hepatic disease or coagulation diseases or disorders.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. Effective doses of the compounds herein are selected to deliver pharmaceutically effective amounts of the parent compound when converted in vivo. Effective administration of the compounds of this invention may be given at an oral dose to provided effective pharmaceutical doses of compound 1 of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the recipient's bloodstream, including orally, via implants, parentally (including intravenous, intraperitoneal, intraarticularly and subcutaneous injections), rectally, intranasally, topically, ocularly (via eye drops), vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

All references, including but not limited to articles, texts, patents, patent applications, and books, cited herein are hereby incorporated by reference in their entirety.

What is claimed is:

1. A compound of formula II

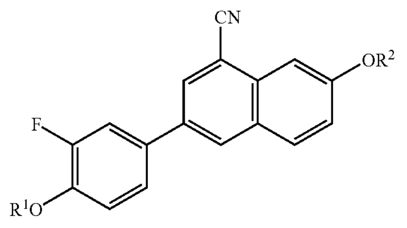

II wherein each $R^1$, and $R^2$ is independently selected from H and —P(O)($R^3$)($R^4$), provided that at least one of $R^1$ and $R^2$ is —P(O)($R^3$)($R^4$);

each $R^3$, and $R^4$ is independently selected from the group consisting of H, —OH, $C_1$-$C_6$ alkyl, and $C_1$-$C_6$ alkoxy;

or a pharmaceutically acceptable salt thereof.

2. The compound of claim 1, wherein each of $R^1$ and $R^2$ is —P(O)($R^3$)($R^4$).

3. The compound of claim 1, wherein each $R^3$ and $R^4$ is —OH.

4. The compound of claim 1, wherein $R^3$ and $R^4$ are independently $C_1$-$C_6$ alkyl or $C_1$-$C_6$ alkoxy.

5. The compound of claim 4, wherein each $R^3$ and $R^4$ are the same.

6. A pharmaceutical composition comprising a compound of formula II

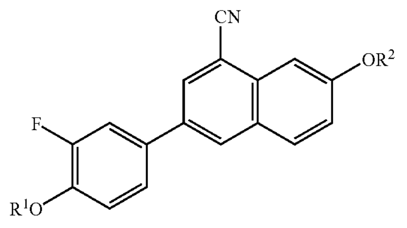

II wherein each $R^1$, and $R^2$ is independently selected from H and —P(O)($R^3$)($R^4$), provided that at least one of $R^1$ and $R^2$ is —P(O)($R^3$)($R^4$);

each $R^3$, and $R^4$ is independently selected from the group consisting of H, —OH, $C_1$-$C_6$ alkyl, and $C_1$-$C_6$ alkoxy;

or a pharmaceutically acceptable salt thereof; and a pharmaceutically acceptable carrier or excipient.

7. The composition of claim 6, wherein each of $R^1$ and $R^2$ is —P(O)($R^3$)($R^4$).

8. The composition of claim 6, wherein each $R^3$ and $R^4$ is —OH.

9. The composition of claim 6, wherein $R^3$ and $R^4$ are independently $C_1$-$C_6$ alkyl or $C_1$-$C_6$ alkoxy.

10. The composition of claim 9, wherein each $R^3$ and $R^4$ are the same.

11. A method of administering a compound of formula I

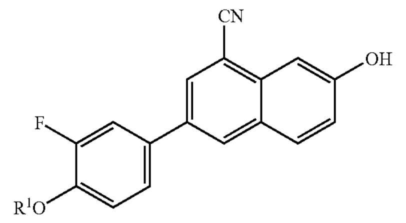

comprising administering to a patient in need thereof a pharmaceutically effective amount of a compound of formula II

II

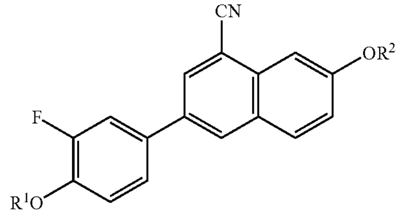

wherein each $R^1$, and $R^2$ is independently selected from H and —P(O)($R^3$)($R^4$), provided that at least one of $R^1$ and $R^2$ is —P(O)($R^3$)($R^4$);

each $R^3$, and $R^4$ is independently selected from the group consisting of H, —OH, $C_1$-$C_6$ alkyl, and $C_1$-$C_6$ alkoxy;

or a pharmaceutically acceptable salt thereof.

12. The compound of claim 11, wherein each of $R^1$ and $R^2$ is —P(O)($R^3$)($R^4$).

13. The compound of claim 11, wherein each $R^3$ and $R^4$ is —OH.

14. The compound of claim 11, wherein $R^3$ and $R^4$ are independently $C_1$-$C_6$ alkyl or $C_1$-$C_6$ alkoxy.

15. The compound of claim 14, wherein each $R^3$ and $R^4$ are the same.

16. A method for preparing compounds of formula II, comprising:

dissolving a compound of formula 1

I

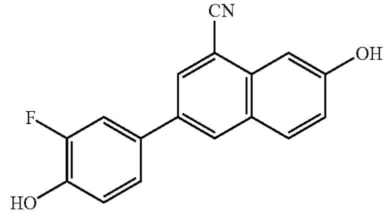

and tetrazole in an organic solvent or mixture of solvents;

adding a diisopropyl-phosphoramidite;

adding 30% hydrogen peroxide;

reducing excess hydrogen peroxide;

extracting the reaction mixture to produce an intermediate;

reacting said intermediate with ethyl acetetate and HCl to obtain the desired product.

17. The method of claim 16, wherein said diisopropyl-phosphoramidite is di-tert-butyl diisopropyl-phosphoramidite.

18. The method of claim 16, wherein said organic solvent or mixture of solvents is a mixture of tetrahydrofuran and methylene chloride.

19. The method of claim 18, wherein said mixture is a 1:1 mixture of tetrahydrofuran and methylene chloride.

20. A method of making compounds of formula I wherein $R^1$ and $R^2$ are both $PO(OH)_2$, comprising:

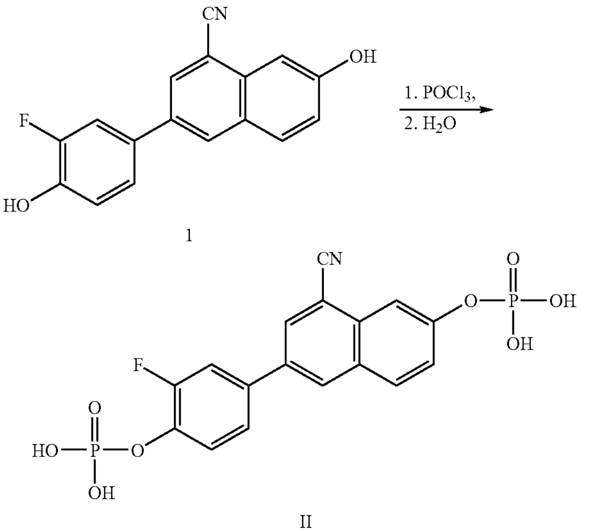

dissolving a compound of formula 1 and pyridine in an organic solvent;

adding resultant solution to cold (0° C.) phosphorous oxychloride.

21. The method of claim 20, wherein said organic solvent is dichloromethane.

22. A method of preparing a monophosphate compound of formula I, comprising:

dissolving diphosphate compound 3

II

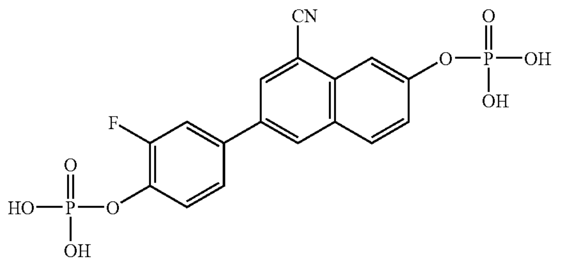

in water;

adding alkaline phosphatase enzyme gradually.

23. A method for treating sepsis in a patient in need thereof, comprising administering a pharmaceutically effective amount of a compound according to claim 1 or a pharmaceutically acceptable salt thereof.

24. A method for treating rheumatoid arthritis in a patient in need thereof, comprising administering a pharmaceutically effective amount of a compound according to claim 1 or a pharmaceutically acceptable salt thereof.

25. A method for treating endometriosis in a patient in need thereof, comprising administering a pharmaceutically effective amount of a compound according to claim 1 or a pharmaceutically acceptable salt thereof.

26. A method for treating fibroids in a patient in need thereof, comprising administering a pharmaceutically effective amount of a compound according to claim 1 or a pharmaceutically acceptable salt thereof.

* * * * *